United States Patent [19]
Shastri et al.

[11] Patent Number: 6,095,148
[45] Date of Patent: *Aug. 1, 2000

[54] NEURONAL STIMULATION USING ELECTRICALLY CONDUCTING POLYMERS

[75] Inventors: Venkatram R. Shastri, Allston; Christine E. Schmidt, Boston; Robert S. Langer, Newton; Joseph P. Vacanti, Winchester, all of Mass.

[73] Assignees: Children's Medical Center Corporation, Boston; Massachusetts Institute of Technology, Cambridge, both of Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/552,761

[22] Filed: Nov. 3, 1995

[51] Int. Cl.$^7$ .................................................. A61B 19/00
[52] U.S. Cl. ........................... 128/898; 607/50; 607/116; 607/117
[58] Field of Search .............................. 607/50, 115, 116, 607/117, 118; 128/898

[56] References Cited

U.S. PATENT DOCUMENTS

| | | | |
|---|---|---|---|
| 3,654,933 | 4/1972 | Hagfors | 607/118 |
| 4,341,221 | 7/1982 | Testerman | 600/377 |
| 4,779,630 | 10/1988 | Scharnberg et al. | 607/142 |
| 4,919,140 | 4/1990 | Borgens et al. | 607/50 |
| 4,983,322 | 1/1991 | Elsenbaumer . | |
| 5,073,114 | 12/1991 | Detsch | 433/228.1 |
| 5,130,412 | 7/1992 | Wellinghoff et al. | 528/341 |
| 5,330,520 | 7/1994 | Maddison et al. | 607/122 |

FOREIGN PATENT DOCUMENTS

| | | |
|---|---|---|
| 40 26978 A1 | 2/1992 | Germany . |
| WO 88/03785 A1 | 6/1988 | WIPO . |
| WO 89/03876 A1 | 5/1989 | WIPO . |
| WO 92/07318 A1 | 4/1992 | WIPO . |
| WO 92/11644 A1 | 7/1992 | WIPO . |
| WO 94/07182 A1 | 3/1994 | WIPO . |

OTHER PUBLICATIONS

Aebischer, et al., "Piezoelectric guidance channels enhance regeneration in the mouse sciatic nerve after axotomy," *Brain Res.* 436(1):165–168 (1987).

Andreatta, et al., "Processing of Conductive Polyaniline–UHMW Polyethylene Blends from Solutions in Non–Polar Solvents," *Synth. Met.* 55(2 and 3):1017–1022 (1993).

Armes, "Optimum Reaction Conditions For the Polymerization of Pyrrole by Iron(III) Chloride in Aequeous Solution," *Synth. Met.* 20(3):365–371 (1987).

Brédas, et al., eds. *Conjugated Polymeric Materials: Opportunities in Electronics, Optoelectronics, and Molecular Engineering*, (Kluwer Academic Publisher, Dordrecht, 1991) (Table of Contents only).

(List continued on next page.)

*Primary Examiner*—Linda C. M. Dvorak
*Assistant Examiner*—R Kearney
*Attorney, Agent, or Firm*—Mary Rose Scozzafava; Clark & Elbing LLP

[57] ABSTRACT

Methods and support systems are provided for modifying the regeneration, differentiation, or function of cells. In one embodiment, electrically conducting biocompatible polymers may be used alone or in combination with a polymeric support for in vitro nerve cell regeneration, or in vivo to aid in healing nervous tissue defects. The conductive polymers may implanted adjacent to or seeded with nerve cells. Voltage or current is applied to the polymer in a range which induces the desired effect on the cells while not damaging the cells. The methods and systems can be used in a variety of applications to enhance in vivo or in vitro growth or regeneration of nervous tissue.

26 Claims, 4 Drawing Sheets

OTHER PUBLICATIONS

Cao, et al., "Magnetic susceptibility of polyaniline in solution in non–polar organic solvents and in polyblends in poly(methyl methacrylate)," *Synth. Met.* 52:193–200 (1992).

Cao, et al., "Counter–ion induced processibility of conducting polyaniline and of conducting polyblends of polyaniline in bulk polymers," *Synth. Met.* 48:91–97 (1992).

Couves, et al., "Polypyrrole as a Potentiometric Glucose Sensor," *Synt. Met.* 28:C761–C768 (1989).

Decher, et al., "Buildup of ultrathin multilayer films by self–assembly process: III. consecutively alternating absorption of anionic and cationic polyelectrolytes on charged surfaces," *Thin Solid Films* 210/211(1 and 2):831–835 (1992).

Diaz, et al., "Electrochemistry of Conducting Polypyrrole Films," *J. Electroanal. Chem.*, 129:115–132 (1981).

Greene, et al., "Establishment of a noradrenergic clonal line of rat adrenal pheochromocytoma cells which respond to nerve growth factor," *Proc. Natl. Acad. Sci., USA* 73(7):2424–2428 (1976).

Hu, "RNA Synthesis in Peripheral Nerve in the Chick During Development," *Can. J. Biochem.* 49:320–327 (1971).

Jaffe, et al., "Neurites Grow Faster Towards the Cathode than the Anode in a Steady Field," *J. Exp. Zool.* 209:115–127 (1979).

Kanatzidis, "Conductive Polymers," *Chem. Eng. News* 68:36–54 (1990).

Kerns, et al., "Electrical Stimulation of Nerve Regenration in the Rat: The Early Effects Evaluated By a Vibrating Probe and Electron Microscopy," *Neuroscience* 40(1):93–107 (1991).

Langer, et al., "Selective Cell Transplantation Using Bioabsorbable Artificial Polymers as Matrices," *J. Ped. Surg.* 23(1):3–9 (1988).

Lavine, et al., "Current Concepts Review Electrical Stimulation of Repair of Bone," *J. of Bone and Joint Surgery* 69–A:625–630 (1987).

Liao, et al., "Polymeric Dopants for Polyaniline," *PSME Preprints* Abstract No. 162 ACS Meeting, Chicago, (Aug. 1993).

Luther, et al., "Changes in cell shape and actin distribution induced by constant electric fields," *Nature* 303(5912):61–64 (1983).

Malhotra, et al., "Polyaniline/Polymeric Acid Composite, a Novel Conducting Rubber," *J. Appl. Polym. Sci.* 40(5 and 6):1049–1052 (1990).

Miller, ed., *Extended Linear Chain Compounds*, vol. 1, (Plenum Press, New York, 1983) (Table of Contents only).

Miller, L.L., "Electrochemically Controlled Release of Drug Ions from Conducting Polymers," *Mol. Cryst. Liq. Cryst.* 160:297–301 (1988).

Miller, et al., "Poly(N–methylpyrrolylium) Poly(styrenesulfonate). A Conductive, Electrically Switchable Cation Exchanger That Cathodically Binds and Anodically Releases Dopamine," *Macromolecules* 20:1594–1597 (1987).

Minehan, et al., "Kinetics of DNA Binding to Polypyrrole," *Polym. Mat. Sci. Eng.*, 64:341–342 (1991).

Myers, "Chemical Oxidative Polymerization as a Synthetic Route to Electrically Conducting Polypyrroles," *J. Electron. Mater.* 15:61–69 (1986).

Patel, et al., "Perturbation of the Direction of Neurite Growth by Pulsed and Focal Electric Fields," *J. Neurosc.* 4(12):2939–2947 (1984).

Politis, et al., "Mammalian Optic Nerve Regeneration Following the Application of Electric Fields," *J. Trauma* 28(11):1548–1552 (1988).

Prezyna, et al., "Interaction of Cationic Polypeptides and Electroactive Polypyrrole/Poly(styrenesulfonate) and Poly(N–methylpyrrole)/ Poly(styrenesulfonate) Films," *Macromolecules* 24(19):5283–5287 (1991).

Sadik, et al., "Pulsed amperometric detection of proteins using antibody containing conducting polymers," *Analytica. Chimica. Acta.* 279:209–212 (1993).

Shastri, "Evaluation of Polypyrrole Thin Films of Substratum for Mammalian Cell Culture," *Dissertation Abstracts International*, vol. 56/09–B, p. 4911 (Rensselaer Polytechnic Institute, 1995) (Abstract).

Shibib, et al., "Polarization of Nerve Regeneration (Electrotaxis)," *Surg. Neurol.* 29(5):372–388 (1988).

Shinohar, et al., "Electrically stimulated rupture of cell membranes with a conducting polymer–coated electrode," *Biolectrochemistry and Bioenergetics* 22:23–35 (1989).

Sisken, et al., "Stimulation of rat sciatic nerve regeneration with pulsed electromagnetic fields," *Brain. Res.* 485(2):309–316 (1989).

Smith, et al., "Investigation of the Relationship Between Conductivity and Protein–Binding Properties of Polypyrrole," *J. Appl. Polym. Sci.* 43(2):399–403 (1991).

Street, *Handbook of Conducting Polymers*, vol. 1 (Skotheim, ed.) (Marcel Dekker, Inc., New York) (Table of Contents).

Street, "Polypyrrole From Powers to Plastics," Chapter 8, (Marcel Dekker, Inc., New York) (Table of Contents).

Street, et al., "Conducting Polymers: A Review of Recent Work," *IBM J. Res. Develop.* 25(1):51–57 (1981).

Trivedi, et al., "Investigations on the effect of 5–sulfosalicylic acid on the properties of polyaniline," *Synth. Met.* 58(3):309–324 (1993).

Umaña, et al., "Protein–Modified Electrodes. The Glucose Oxidase/Polypyrrole System," *Anal. Chem.* 58:2979–2983 (1986).

Valentini, et al., "Electrically charged polymeric substrates enhance nerve fibre outgrowth in vitro," *Biomaterials* 13(3):183–190 (1992).

Valentini, et al., "Polymer electret guidance channels enhance peripheral nerve regeneration in mice," *Brain. Res.* 480(1/2):300–304 (1989).

Wallace, et al., "Preparation and Application of Conducting Polymers Containing Chemically Active Counterions for Analytical Purposes," *J. Electroanal. Chem.* 247(1 and 2):145–156 (1988).

Wong, et al., Electrically conducting polymers can noninvasively control the shape and growth of mammalian cells, *Proc. Natl. Acad. Sci., USA.* 91:3201–3204 (1994).

Yang, et al., *Polymer Preprints*, ACS Meeting, 34(1) (Denver, Mar. 1993) (List of Attendees).

Yang, et al., "Processable conductive composites of polyaniline/poly(alkyl methacrylate) prepared via an emulsion method," *Synth. Met.* 59(1):1–12 (1993).

Yaoita, et al., "Electrically Regulated Cellular Morphological and Cytoskeletal Changes On An Optically Transparent Electrode (With 1 Color Plate)", *Exptl. Cell Biol.* 57:43–51 (1989).

NEURONAL STIMULATION USING ELECTRICALLY CONDUCTING POLYMERS

BACKGROUND OF THE INVENTION

The present invention relates to methods for stimulating nerve cells, and more specifically, to methods for promoting attachment, proliferation and differentiation of nerve cells by electrical stimulation of the cells on electrically conducting polymers.

The development of methods for promoting the growth and differentiation of nerve cells has proved to be very difficult. Neurons have been found to have only a limited ability to regenerate. After about six months, most nerve cells lose their ability to reproduce, and the ability of damaged nerve cells to repair themselves is very limited. There also are few methods available for the stimulation of neuron extension and differentiation in vitro or in vivo.

Electrical charges have been found to play a role in enhancement of neurite extension in vitro and nerve regeneration in vivo. Examples of conditions that stimulate nerve regeneration include piezoelectric materials and electrets, exogenous DC electric fields, pulsed electromagnetic fields, and direct application of current across the regenerating nerve. Neurite outgrowth has been shown to be enhanced on piezoelectric materials such as poled polyvinylidinedifluoride (PVDF) (Aebischer et al., Brain Res., 436;165 (1987); and R. F. Valentini et al., Biomaterials, 13:183 (1992)) and electrets such as poled polytetrafluoroethylene (PTFE) (R. F. Valentini et al., Brain. Res. 480:300 (1989)). This effect has been attributed to the presence of transient surface charges in the material which appear when the material is subjected to minute mechanical stresses. Electromagnetic fields also have been shown to be important in neurite extension and regeneration of transected nerve ends. R. F. Valentini et al., Brain. Res., 480:300 (1989); J. M. Kerns et al., Neuroscience 40:93 (1991); M. J. Politis et al., J. Trauma, 28:1548 (1988); and B. F. Sisken et al., Brain. Res., 485:309 (1989). Surface charge density and substrate wettability have also been shown to affect nerve regeneration. Valentini et al., Brain Res., 480:300–304 (1989).

Neurites have been shown to preferentially migrate toward the cathode under steady electric fields. L. F. Jaffe and M. -M. Poo., J. Exp. Zool., 209:115 (1979); N. B. Patel and M. -M. Poo, J. Neurosc., 4:2939 (1984); and K. Shibib et al., Surg. Neurol., 29:372 (1988). Mechanisms for the observed effects which have been proposed include redistribution of cytoskeletal proteins such as actin (P. W. Luther et al., Nature, 303:61 (1983)), and other molecules (M. J. Politis et al., J. Trauma, 28:1548 (1988)), favorable protein conformational changes (R. F. Valentini et al., Biomaterials, 13:83 (1992)), and promotion of electrical communication between nerve stumps (K. Shibib et al., Surg. Neurol., 29:372 (1988)).

There are several drawbacks to these systems. In the case of the PVDF and PTFE systems, the polymers have to be poled (alignment of dipoles) for several hours above the glass transition temperature of the polymer in the presence of high electric fields of approximately 21 Kv. It is only after poling that these materials exhibit strong piezoelectric or electret behavior for finite lengths of time. In the systems which utilize application of electromagnetic fields (exogenous and in vivo) for neuronal stimulation, the applied field is not focused on neuronal tissue but rather broadly applied over the entire site of the injury.

Polypyrrole (PP) has been used in a matrix for controlled delivery of the neurotransmitter dopamine (L. L. Miller and Q. -X. Zhou, Macromolecules, 20:1594 (1987)) and as a biosensor for detection of glucose (L. D. Couves, Synt. Metals., 28:C761 (1989)) or other proteins (O. A. Sadik and G. G. Wallace, Analytica. Chimica. Acta., 279:209 (1993)). Cell-surface surface interactions and cellular functions have been shown to be controlled on PP thin films by either changing the oxidation state of the polymer (J. Y. Wong et al., Proc. Natl. Acad. Sci., USA., 91:3201 (1994)) or by changing the wettability of the polymer film using appropriate dopants (V. R. Shastri, Ph.D. Dissertation Rensselaer Polytechnic Institute, 1995).

There is a need for the development of materials for controlling nerve cell attachment, growth and regeneration, both in vitro and in vivo, which would permit in vitro cultivation of nerve cells over a prolonged period of time and manipulation of in vivo regeneration, differentiation and function of nerve cells.

It is therefore an object of the present invention to provide methods and compositions for stimulating the attachment and regeneration of cells including nerve cells in culture. It is another object of the present invention to provide methods and compositions for enhancing growth and regeneration of cells including nerve cells when implanted in vivo on artificial substrates and prostheses. It is a further object of the present invention to provide methods and compositions which can potentially be used to stimulate attachment and growth of nerve cells in vivo, thereby to permit repair of nerve damage, reconstruction of nerve tissue and replacement of lost nerve system function.

SUMMARY OF THE INVENTION

Described are methods and support systems for modifying the regeneration, differentiation, or function of cells both in vivo and in vitro. In one embodiment, electrically conducting biocompatible polymers may be used alone or in combination with polymeric supports which are used in vitro for nerve cell growth, or in vivo to aid in healing nervous tissue defects. The conducting polymers may be implanted adjacent to or seeded with cells which are to be affected. Voltage or current may be applied to the polymer in a range which induces the desired effect on the cells while not damaging the cells. In a preferred embodiment, the conducting polymers include polypyrroles which are easy to prepare and permit focused neuronal stimulation.

DETAILED DESCRIPTION OF THE INVENTION

Figure 1:
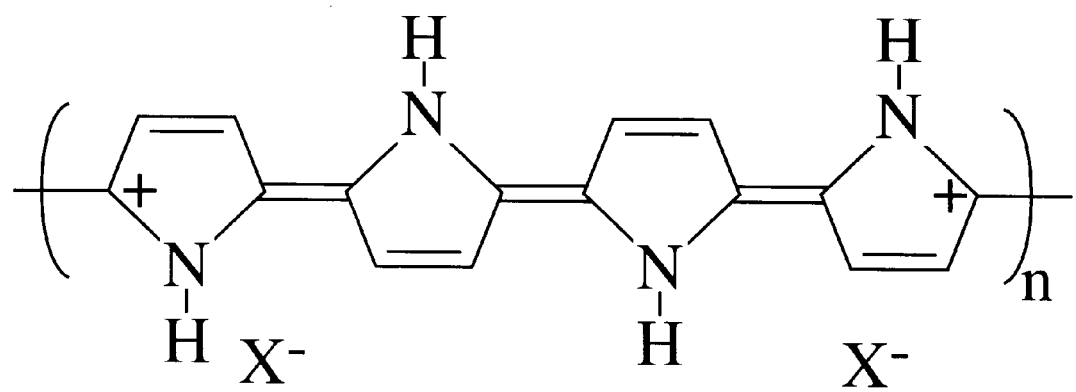
FIG. 1 is an illustration of the structure of polypyrrole in the oxidized state, where X is a dopant anion.

Methods and systems are provided for altering the regeneration, differentiation, or function of cells including nerve cells in vitro and in vivo. In one embodiment, methods and systems are provided which permit the attachment and regeneration of cells such as nerve cells attached to or in proximity with electrically conducting polymers. Optionally, a voltage or current can be applied to the polymer to enhance the effect. Cell functions such as adhesion, proliferation (i.e., migration and growth) and regeneration (e.g, neurite extension and cell spreading) can be altered. Surfaces formed of electrically conducting polymers are advantageous in that their properties, including surface charge, wettability, conformational and dimensional changes, can be altered reversibly by oxidation or reduction. The polymers are applied as coatings to substrates or used to form polymeric substrates to which the cells are attached, either directly or via attachment molecules, and regenerated, either in vitro or in vivo. The amount of voltage (voltage x time of application) or current applied to the polymer can determine the effect on the cells.

I. Substrates

A. Electrically Conducting Polymers.

Conjugated polymers represent a relatively new class of materials whose electrical and optical properties can be controllably varied over an extremely wide range, oftentimes in a completely reversible manner. This is typically accomplished either by chemical or electrochemical oxidation of the π-system of the polymer backbone or, in some cases, by direct protonation of the polymer backbone. Through this chemical "doping" process, it is possible to systematically vary the electrical conductivity of these materials from the insulating state to the conducting state. The electrically conducting forms of these materials are best described as p-type doped polymeric charge transfer salts in which the conjugated polymer supports positive charges that are delocalized over relatively short segments of the backbone, for example, over three to four repeating units for a highly oxidized polymer. Charge neutrality is maintained by a negatively charged counterion, which is usually derived from the doping agent.

The positively charged defect states created on the polymer backbone by the doping process can exist in many different forms, including as polarons (coupled radical cations), bipolarons (coupled dications) and solitons (noninteracting cations). These charged defect states are believed to be the primary charge carriers in these materials and are therefore responsible for their electrically conducting nature.

An electrically conducting polymer is a conjugated polymer which can be reversibly oxidized and reduced. Representative electrically conducting polymers include polyacetylene, polyaniline, polypyrrole, polythiophene, poly(phenylenesulfide), and poly(phenylenevinylene), among many others. Kanatzidis, M. G. *Chem, Eng. News*, 68, 36–54 (1990); and Street, G. B.; Clarke, T. C. *IBM J. Res. Develop.*, 25, 51–57 (1981). Polymers can be deposited as coatings onto substrates or polymerized to form objects. Polymers can be applied as a single layer coating of a single polymer or as a multilayered film to alter the properties of the applied polymers.

Conducting polymers can be in the form of conjugated polyions or nonderivatized conjugated polymers. Nonderivatized conjugated polymers, i.e., those that do not include ionizable sidegroups, are significantly more environmentally stable than their derivatized polyion counterparts and also have been found to exhibit much higher electrical conductivities. Examples of nonderivatized conjugated polymers can be found in "*Conjugated Polymeric Materials. Opportunities in Electronics, Optoelectronics, and Molecular Engineering*", J. L. Bredas and B. Silbey, Eds., Kluwer, Dordrecht, 1991, the disclosure of which is incorporated herein by reference.

In a preferred embodiment, electrically conductive polymers which can be used include polyanilines, polypyrroles and polythiophenes. As defined herein, the terms "polyanilines", "polypyrroles" and "polythiophenes," includes polyaniline, polypyrrole, polythiophenes, and derivatives thereof, which can be made using methods available in the art. Derivatives which can be used include substituted polyanilines, polypyrroles and polythiophenes, such as N-substituted polypyrroles. Additionally, 3-substituted polyanilines, polypyrroles, and polythiophenes can be used, such as 3-alkyl substituted derivatives.

In a preferred embodiment, the conducting polymer is polypyrrole, which is useful because of its inherent electrical conducting properties. FIG. 1 shows the chemical structure of electrochemically synthesized polypyrrole in the oxidized state (PP$^+$). The highly conjugated backbone permits electron transfer between different chains, giving rise to electronic conduction. X$^-$ is a negatively charged counter ion (dopant) that associates with polycationic polypyrrole to yield overall charge neutrality. Dopants which can be utilized include poly(styrenesulfonate) (PSS$^-$), dextran sulfate, chondroitin sulfates (e.g., chondroitin sulfate A, B and C), heparin and other sulfonated biological molecules. Polycations may be absorbed or attached to the doped conducting polymer surface, such as polylysine, collagen and fibronectin to modify the charge of the surface.

PP exhibits reversible electrochemistry. This permits the control of the surface charge density by varying the oxidation state of the polymer. The ability to vary surface properties and hence cell-substrate interactions by choice of dopant or by varying its oxidation state makes polypyrrole (PP) very useful for tissue engineering applications.

Polyaniline (PAn) doped with functionalized sulfonic acids also may be used. Several research groups have reported approaches to process doped PAn; both homopolymer films, as well as conducting blends. For example, the use of "functionalized" protonic acids, primarily large sulfonic acids as PAn dopants, renders the doped polymer soluble in several organic solvents, [C. Y. Yang, et al., *Polymer Preprints*, ACS Meeting, Denver, March 1993; Y. Cao and A. J. Heeger, *Synth. Met.*, 52, 193 (1992); Y. Cao, P. Smith and A. J. Heeger, *Synth. Met.*, 48 (1992), 91; A. Andreatta and P. Smith, *Synth. Met.*, 55, 1017 (1993)1. Blends with several host polymers have been reported, including polymethylmethacrylate (PMMA), nylon, polyvinylchloride (PVC), polystyrene (PS), polyvinyl acetate (PVA), polypropylene, polyethylene (PE), ABS, and polycarbonate [Y. Cao, P. Smith and A. J. Heeger, *Synth. Met.*, 48, 91 (1992); A. Andreatta and P. Smith, *Synth. Met.*, 55, 1017 (1993)]. Conducting PAn/poly (alkyl methacrylate) blends have been prepared by emulsion polymerization in the presence of HCI [S. Y. Yang and E. Ruckenstein, *Synth. Met.*, 59 (1993)]. Conducting PAn films have been cast from a ferric chloride solution in nitromethane, starting with either PAn base or already-doped PAn, as described by U.S. Pat. No. 4,983,322 to Elsenbaumer. Doped PAn can also be solubilized by the addition of a Lewis base which acts to complex the dopant, rendering the PAn soluble, as described in International Patent Application, No. WO92/11644 by Han, et al., (1992). PAn doped with 5-sulfosalicylic acid (SSA) is soluble in DMSO, dimethylformamide (DMF), and NMP, as reported by D. C. Trivedi and S. K. Dhawan, *Synth. Met.,* 58, 309 (1993). Two groups have reported doping PAn with a polymeric dopant, sulfonated polystyrene: Y. -H. Liao and K. Levon, *PSME Preprints,* ACS Meeting, Chicago, August 1993; and B. D. Malhotra, et al.,*J. Appl. Polym. Sci.,* 40, 1049 (1990).

B. Preparation of Conductive Polymer Materials

The methods of synthesis and application for polypyrrole are typical of those for other electrically conducting polymers. Polypyrrole is perhaps the most widely studied electrically conducting polymer due to its chemical and thermal stability, ease of preparation, and electroactivity. Street, G. B. in *Handbook of Conducting Polymers*; Skotheim, T. A.; Marcel Dekker, Inc., New York, 1986; pp 265. Polypyrrole has been used in biological environments as biosensors (Umana, M.; Waller,*J. Anal. Chem.,* 58, 2979–2983) (1986); electrodes to obtain electrochemically controlled drug release (Miller, L. L. *Mol. Cryst. Liq. Cryst.,* 160, 297) (1988); as substrates which bind proteins (Prezyna, L. A.; Qiu, Y. J.; Reynolds, J. R.; Wnek, G. E. *Macromolecules,* 24, 5283–5287 (1991); Smith, A. B.; Knowles, C. J. *J. Appl. Polym. Sci.,* 43, 399–403 (1991); Wallace, G. G.; Lin, Y. P. *J. Electroanal. Chem.,* 247, 145–156 (1988)) and DNA; Minehan, D. S.; Marx, K. A.; Tripathy, S. K. *Polym. Mat. Sci. Eng.,* 64, 341–2 (1991); and to burst cells associated with the polymer M. Yaoita et al.,*Exptl. Cell Biol.,* 57:43–51 (1989); H. Shinohar et al., *Bioelectrochemistry and Bioenergetics,* 22:23–35 (1989), a section of *J. Electroanal. Chem.,* vol. 276 (Elsevier Sequoia S.A. Lausanne, Netherlands 1989).

Pyrrole can be either chemically or electrochemically polymerized to form polypyrrole. The chemical synthesis of polypyrrole in aqueous solution can be carried out by the method of S. P. Armes, *Synth. Met.,* 20, p. 365 (1987) and A. B. Smith and C. J. Knowles, *J. Appl. Polym. Sci., pp.* 399–403, vol. 43, No. 2, Jul. 20, 1991. Briefly, anhydrous ferric chloride, e.g., 36 g., is dissolved in 400 mL double distilled water and cooled to 0° in an ice bath. Distilled pyrrole, (4 mL), precooled to 0° C., is added to the solution of ferric chloride with vigorous stirring for at least 2 hours. The insoluble polymer that forms is filtered on Whatman No. 6 filter membrane (Whatman Inc., Clifton, N.J. 07014) and washed extensively with water until a clear solution is obtained. It is further rinsed with ethanol and finally with diethyl ether before overnight drying at 35° C.

Chemical synthesis of polypyrrole in organic solvent can be carried out by the method of R. E. Myers, *J. Electron. Mater.,* 15, p. 61 (1986), and A. B. Smith and C. J. Knowles, *J. Appl. Polym. Sci., pp.* 399–403, vol. 43, No. 2, Jul. 20, 1991. Diethyl ether (300 mL) is added to 19.6 g of anhydrous ferric chloride contained in a 500 mL beaker. Cold distilled pyrrole (2.1 mL) is added to the stirred ferric chloride/ether solution precooled to 0° C. and stirred at this temperature for at least 1 hour. The insoluble product is recovered, washed and dried as described above.

In a preferred embodiment, PP films may be synthesized electrochemically. Electrochemical synthesis of polypyrrole films can be carried out, for example, by the electrooxidation of pyrrole in a one-compartment cell equipped with a platinum working electrode, gold wire counter electrode, and a sodium chloride calomel reference electrode. In a typical preparation, an acetonitrile solution containing 0.1 M tetraethylammonium tetrafluoroborate plus about 0.02 M pyrrole is employed, as described by Diaz, A. F.; Kanazawa, K. K. *Extended Linear Chain Compounds*; Plenum Press, New York, 1983 pp. 417–441. The oxygen in the solution is swept out with an inert gas prior to the electrolysis. In practice, a wide variety of solvents and electrolytes can be used as long as the electrical resistance of the solution is not high and the nucleophilicity does not interfere with the polymerization reaction.

Additionally, PP films can be synthesized electrochemically, as described below in Example 1, using Indium Tin Oxide (ITO) conductive borosilicate glass (Delta Technologies, Still Water, Minn.) as the electrically conductive surface for the PP film deposition, using a three electrode setup with: the ITO glass as the working electrode, a platinum gauze as the counter electrode, and an Ag/AgCl electrode as a reference. PP film may be electrochemically deposited onto the ITO glass (working electrode), for example, at a constant potential of 0.7 volts from an aqueous solution of 0.1 M pyrrole containing 0.1 M sodium salt of poly(styrenesulfonate). The sodium salt of poly (styrenesulfonate) thus may serve as both the dopant and electrolyte. Other dopants which may be used include dextran sulfate, chondroitin sulfates, heparin and sulfonated biological molecules.

Conducting polypyrrole (PP) films of varying thicknesses may be synthesized, for example, thin films on the order of between about 0.1 and 0.15 $\mu$m and thick films, on the order of between about 1.8 and 2.0 $\mu$m. The film thickness may be controlled by the passage of charge (A. F. Diaz et al., *J. Electroanal. Chem.,* 129:115 (1981)). For example, a charge of 26.2 mCol/cm$^2$ yields a PP film of approximately 0.1 $\mu$m in thickness. The amount of charge passed during the film synthesis may be determined from the area under the curve of a plot of current versus time, or voltage versus time when you use a time based recorder. Methods for the synthesis of optically transparent PP thin films are described in: J. Y. Wong et al., *Proc. Natl. Acad. Sci., USA.,* 91:3201–3204 (1994), the disclosure of which is incorporated herein by reference.

C. Multilayer Films

Methods for the preparation of ultrathin multilayered films available in the art may be used including: solution casting, Langmuir-Blodgett technique, chemisorption, the method of Decher et al., Thin Solid Films 210/211, 831 (1992) and the method of Rubner et al., PCT/US94/07182 by Massachusetts Institutes of Technology Solution casting of preformed bilayer aggregates and annealing of spin coated films of copolymers yields layered structures, although alignment of the layers and the positioning of molecules with respect to each other is limited. In the Langmuir-Blodgett (LB) technique, a film is prepared on the surface of water and then transferred onto solid substrates. This method, however, is generally only applicable to flat substrates. Another method is based on chemisorption.

Decher et al., *Thin Solid Films* 210/211, 831 (1992) and DE 4026978 (WO92-073188/10), have demonstrated that it is possible to build up multilayer thin films of polymers onto charged surfaces via the alternating deposition of polycations and polyanions. The basis for this multilayer assembly process is the ionic attraction of the permanently fixed charges that exist on the polycations (positive charge) and polyanions (negative charge). In essence, the excess charge of a polyion adsorbed onto a substrate surface is used to attract a polyion of the opposite charge onto the surface. Multilayer thin films are fabricated by simply alternating the dipping process.

This approach can be used to manipulate a variety of different polyions, including conjugated polyions (conjugated polymers fitted with ionizable sidegroups), which function as conducting polymers. However, the addition of ionizable sidegroups to the repeat structure of a conjugated polymer can compromise the level of conductivity achievable with the polymer. It is therefore more desirable and useful to be able to fabricate more conventional conjugated polymers such as polyaniline and polypyrrole into ultrathin multilayer thin films.

Milliken Corp. has disclosed a procedure for coating various textile fibers with uniform, electrically conducting films of polypyrrole and polyaniline. Specifically, the deposition of an electrically conducting coating of polypyrrole onto the fibers is accomplished by placing the fibers into a dilute aqueous solution of pyrrole that also contains an oxidizing agent such as ferric chloride and negative counterions suitable for enhancing the conductivity and conductivity stability of the polymer. The counterions are typically added in the form of sulfonic acids such as naphthalene disulfonic acid. A typical coating solution contains about 10 g/l ferric chloride anhydride, 5 g/l toluenesulfonic acid and 0.2 g of pyrrole monomer.

A useful method for fabricating multilayer thin films with new electrical and optical properties is disclosed by Rubner et al., in PCT/US94/07182 by Massachusetts Institutes of Technology, which utilizes a molecular-level, layer-by-layer deposition process. This process is especially useful for the construction of heterostructure thin films with complex molecular architectures and thicknesses that are controllable at the molecular level. The basic process used to create alternating layer thin films involves dipping a substrate into a dilute solution of a p-type doped polymer such as a p-doped conjugated polymer, rinsing the substrate with water (or other solvent for the polymer) and then dipping it into a dilute solution containing a polyanion or a water soluble, non-ionic polymer. This process can be repeated as many times as desired to build multilayer thin films in which each bilayer deposited is only about 10–100 Å in thickness, depending on parameters such as solution concentration, doping level, pH, and ionic strength.

The generation of water soluble, p-type doped conducting polymers can be accomplished in a number of different ways. In one embodiment, conducting polymer chains are formed in situ in a dilute aqueous solution primarily consisting of a monomer and an oxidizing agent. In this case, the conducting polymer is actually created in the solution and subsequently spontaneously adsorbed onto the substrate surface as a uniform, ultra-thin film of between approximately 10 to greater than 250 Å in thickness, more preferably between 10 and 100 Å.

Thin, electrically conducting coatings of polypyrrole and polyaniline, for example, can be formed on various substrates by simply placing the object to be coated in an aqueous bath containing dilute (less than about 0.1 m/l) quantities of pyrrole (or aniline) monomer and a suitable oxidizing agent such as ferric chloride or ammonium peroxysulfate. The use of dilute solutions of the monomer insures that the electrically conductive polymer formed from the oxidative polymerization of the monomer will be deposited exclusively onto the substrate to be coated as opposed to simply polymerizing in the solution and precipitating out as an insoluble powder.

Highly uniform and dense multilayer thin films can be easily fabricated by simply dipping the substrate into a dilute aqueous solution of a polyanion, whereby a monolayer of this material is deposited onto the p-type doped conducting polymer. This process of alternately depositing layers of a p-type doped polymer and a negatively charged polyanion can be repeated as often as needed to create thin films with precisely controlled thickness and structure.

Alternatively, in a second embodiment, preformed conducting polymers are used directly by forming dilute solutions of their doped forms in suitable solvent systems. In this case, it is necessary to control the type of solvent system used and the level and type of chemical doping of the polymer chains. The general procedure involves first dissolving the undoped polymer in a suitable organic solvent and subsequently diluting this polymer solution with a solvent that contains a dopant for the polymer. This produces a solvent system capable of solvating the doped polymer chains. In the case of polyaniline, for example, it has been found that dilute aqueous solutions can be easily formed by first dissolving the nonconducting emeraldine-base form of this polymer in dimethylacetamide (DMAc) (or n-methyl pyrrolidone) (NMP) and subsequently diluting this solution with acidic water such that the final solution has a 90/10 water to DMAc volume ratio. Since the final step of this process also acid dopes the polymer, the level of doping can be easily adjusted by controlling the pH level of the final dipping solution. Solutions with polyaniline concentrations as high as 0.01 m/l are easily prepared with this procedure. The net result is a stable, water based solution (90% water) of doped polyaniline that is suitable for molecular self-assembly via alternate deposition with polyanions.

II. Polymer Surface Modification

A. Polymer Compositions

The electrically conducting polymer may be applied to or blended with another biocompatible polymeric material, including biodegradable or non-biodegradable polymeric materials, prior to cell growth and attachment prior to in vivo or in vivo use. Thus, the electrically conducting polymer can blended with another polymeric material, applied as a coating on the surface of another material, or be used to form the material itself.

The other polymeric materials which can be blended or coated with the conducting polymers include biocompatible materials which are not biodegradable, such as poly (styrene), poly(esters), polyurethanes, polyureas, poly (ethylene vinyl acetate), poly(propylene), poly (methacrylate), poly(ethylene), poly(ethylene oxide), glass, polysilicates, poly(carbonates), teflon, fluorocarbons, nylon, and silicon rubber. Other useful materials include biocompatible, biodegradable materials such as poly (anhydrides), poly(hydroxy acids) such as poly(glycolic acid) and poly(lactic acid), poly(lactide-co-glycolide), poly (orthoesters), poly(propylfumerate), proteins and polymerized proteins such as collagen, and polysaccharides and polymerized polysaccharides, such as glycosaminoglycans, heparin and combinations thereof.

B. Polymer Structures

In one embodiment, conductive polymer films can be laminated onto or blended with biocompatible biodegradable or non-biodegradable polymers, such as a poly(lactic acid) or poly(lactic-co-glycolic acid) ("PLGA"). For example, PP films may be laminated with PLGA (50:50) films to yield processible and suturable films and tubes. In one exemplary protocol, PLGA films are cast from a solution in chloroform into a glass vessel, and then removed from the vessel by floating them off in water. The free floating films then are air dried. A PP film then is wetted with methylene chloride and layered with a PLGA film of desired thickness. The laminated PP films then are cut into a desired shape for use in applications such as cell growth and implantation to stimulate neuronal regeneration. The laminated films obtained can be processed into suturable tubes or disks which are suitable for implantation in vivo.

Scaffolds for tissue engineering (implantable matrices) can be coated with, or made of, conducting polymers to enhance regeneration, growth or function of implanted cells or cells which migrate into, attach and proliferate within the implanted matrices. Materials which can be used for implantation include sutures, tubes, sheets, adhesion prevention devices (typically films, polymeric coatings applied as liquids which are polymerized in situ, or other physical barriers), and wound healing products (which vary according to the wound to be healed from films and coating to support structures). Both normal and genetically engineered nerve cells optionally can be seeded on the implants, to help replace lost function. L. S. Lavine et al., *J. of Bone and Joint Surgery,* 625–630 (1987), the disclosure of which is incorporated herein by reference, a general review of electrical stimulation for repair of bone, describes a number of devices which can be modified for use with electrically conducting polymers.

As described by Langer et al., *J. Ped. Surg.* 23(1), 3–9 (1988), WO88/03785 and EPA 88900726.6 by Massachusetts Institute of Technology, a matrix for implantation to form new tissue should be a pliable, non-toxic, porous template for vascular ingrowth. The pores should allow vascular ingrowth and the seeding of cells without damage to the cells or patient. These are generally interconnected pores in the range of between approximately 100 and 300 microns. The matrix should be shaped to maximize surface area, to allow adequate diffusion of nutrients and growth factors to the cells. In the preferred embodiment, the matrix is formed of a bioabsorbable, or biodegradable, synthetic polymer such as a polyanhydride, polyorthoester, or polyhydroxy acid such as polylactic acid, polyglycolic acid, and copolymers or blends thereof. Non-degradable materials can also be used to form the matrix. Examples of suitable materials include ethylene vinyl acetate, derivatives of polyvinyl alcohol, teflon, nylon, polymethacrylate and silicon polymers. The preferred non-degradable materials are ethylene vinyl acetate meshes and polyvinyl alcohol sponges. A non-absorbable polyvinyl alcohol sponge is available commercially as Ivalon™, from Unipoint Industries.

Commercially available materials may be used. Polymers for use in the matrix can be characterized for polymer molecular weight by gel permeation chromatography (GPC), glass transition temperature by differential scanning calorimetry (DSC), thermal stability by thermal gravimetric analysis (TGA), bond structure by infrared (IR) spectroscopy, toxicology by initial screening tests involving Ames assays and in vitro teratogenicity assays, and by implantation studies in animals for immunogenicity, inflammation, release and degradation studies.

For in vitro culture, the electrically conducting polymer can be used as a coating on or can blended with polymers forming culture flasks, wells, beads or other culture containers, for example, formed of plastics such as polystyrene, polypropylene, and polyterepthalate.

III. Use of Bioactive or Attachment Molecules

Molecules such as attachment molecules or bioactive molecules such as growth factors can be provided on the conducting polymers, and may be optionally covalently or non-covalently attached to the polymers.

Attachment molecules are defined as any natural or synthetic molecule which is specifically bound by cell surface receptors. These include natural and synthetic molecules having one or more binding sites. Examples of natural molecules are extracellular matrix factors such as fibronectin and laminin. Examples of synthetic molecules are peptides containing the binding sites of fibronectin. In some embodiments, attachment of the cells to the polymer is enhanced by coating the polymers with compounds such as basement membrane components, gelatin, gum arabic, collagens types I, II, III, IV, and V, fibronectin, laminin, glycosaminoglycans, mixtures thereof, and other materials known to those skilled in the art of cell culture. Extracellular matrix molecules (ECM) include compounds such as laminin, fibronectin, thrombospondin, entactin, proteoglycans, glycosaminoglycans and collagen types I through XII. Other natural attachment molecules include simple carbohydrates, complex carbohydrates, asialoglycoproteins, lectins, growth factors, low density lipoproteins, heparin, poly-lysine, thrombin, vitronectin, and fibrinogen. Synthetic molecules include peptides made using conventional methods to incorporate one or more binding sites such as R G D from fibronectin, L I G R K K T from fibronectin and Y I G S R from laminin.

Methods for attaching biological molecules to polymeric substrates available in the art may be used. Methods for applying attachment molecules to substrates include: attachment of molecules to substrate by applying attachment molecules in a solution such as PBS or a high pH, carbonate buffer and adsorption of the molecules to the substrate surface; ionic binding of attachment molecules to substrate; covalent binding of molecules to the substrate surface by chemical reactions using reagents such as glutaraldehyde or carbodiimide; and drying of attachment molecules on the substrate surface.

The concentration of attachment molecules can be adjusted to produce a specific effect. In general, when molecules are applied to a substrate such as polystyrene, approximately 60 to 80% of these molecules will be bound when added at high concentrations; approximately 80 to 95% of these molecules will be bound when added at low concentrations, when a procedure such as the high pH carbonate coating solution containing attachment molecules is applied to a substrate. Efficiencies are lower for procedures when the substrate is not highly reactive.

In one method for applying attachment molecules to substrate, defined densities of purified attachment molecules are placed onto artificial matrices by preincubating the matrices for 24 hours at 4° C. with a pH 9.4 carbonate buffer (15 mM sodium carbonate, 35 mM sodium bicarbonate) containing different concentrations of the attachment molecule. Non-adsorbed molecules are washed free from the matrix prior to use (e.g., cell plating). In another method, adsorption of attachment molecules or other attachment moieties is accomplished using solvents such as phosphate or Hanks-buffered saline, media, acetic acid with ammonium hydroxide vapor neutralization, or organic solvents. In a third method, molecules are dried directly onto the surface of the matrix. In a fourth method, defined densities of attachment molecules are placed on the matrix by chemically cross-linking to reactive side groups present within the matrix. For example, synthetic RGD peptides may be chemically cross-linked to a matrix that contains free amino or carboxyl groups using glutaraldehyde (2% glutaraldehyde by volume in a buffered solution, for example, 0.1 M sodium cacodylate, pH 7.4) or carbodiimides as cross-linker agents. In this method, aqueous solutions containing varying concentrations of purified attachment molecules or other attachment moieties are incubated with the artificial matrices in the presence of a constant amount of glutaraldehyde or carbodiimide.

Appropriate conversions must be made when using small synthetic peptides composed almost entirely of individual binding sites or polymers having multiple binding sites to yield an equivalent density of binding sites. An example of a commercially available synthetic peptide containing a binding site is "Peptite™ 2000", a commercially available form of RGD peptide from Telios Pharmaceuticals that coats onto dishes from phosphate-buffered saline when incubated 24 h at 4° C. Defined densities can be applied as a gradient to achieve more than one effect on the same substrate, i.e., migration and regeneration initially, then differentiation and functioning. Cells can also be cultured on a substrate having attachment molecules at one concentration, then moved to, or overlaid with, substrate having attachment molecules in another concentration.

IV. Cells

The electronically conductive polymers can be used to alter the regeneration, differentiation, or function of cells including endothelial cells, parenchymal cells such as hepatocytes, Islet cells, and other organ cells, muscle cells, cells forming bone and cartilage such as osteoblasts and chondrocytes and nerve cells, from mammalian tissue or lower animals and genetically-engineered cells.

In one embodiment, the regeneration, differentiation, or function of nerve cells can be altered using the electrically conducting polymers. The conditions including time, choice of conducting polymer, and extent of applied voltage or current can be optimized for a particular nerve cell type. Nerve cells obtained by biopsy or cell culture may be cultivated which are obtained from different tissue samples. As defined herein, nerve cells include neurons isolated from tissues such as nerve cells from the central nervous system including brain and spinal cord neurons, and neurons of the peripheral nervous system including sensory and motor neurons, as well as nerve cells obtained from established cell lines and maintained in culture, and recombinant nerve cells. The systems can be used to regenerate and/or proliferate nervous tissue including both nerve cells and the associated neuroglia. The methods and systems permit, for example, the enhancement of nerve cell adhesion and extension of neurites including dendrites and axons.

V. Conditions for Stimulation of Cells

The electrically conducting polymers can be used to alter the regeneration, differentiation, or function of cells in vivo and in vitro, by attaching or abutting the cells to the electrically conductive polymers. Surprisingly, the electrically conducting polymers can be used to alter the regeneration, differentiation, or function of cells even without applying a voltage or current to the polymer. To enhance the effect, a voltage or current is applied to the polymer to which the cells are attached or abutted.

A. In Vitro Conditions

In one embodiment, in in vitro applications, nerve cells, for example, may be cultured by disposing the cells on electrically conducting polymers as described herein, and then stimulating the polymer with an applied voltage or current sufficient to promote in vitro proliferation or regeneration. The conducting polymers may be blended or coated on a polymeric support such as a film or polymeric beads. Cell media available in the art, and other conditions such as temperature, can be optimized for different applications. Exemplary conditions for culturing nerve cells are a medium comprising 85% high-glucose DMEM (GibcoBRL, Grand Island, N.Y.), 10% heat-inactivated horse serum, and 5% fetal bovine serum (FBS). The cells may be "primed" by the addition of nerve growth factor ("NGF"), as described in L. Greene and A. Tischler, *Proc. Natl. Acad. Sci., USA.*, 73:2424 (1976).

Nerve explants also may be cultured and regenerated in vitro for implantation in vivo. For example, primary sciatic nerve explants may be isolated from mammalian tissue and cultured for example in high glucose DMEM supplemented with glucose, fetal bovine serum (FBS), sodium pyruvate, and NGF. Methods for isolating the sciatic nerve from 16-d chick embryos have been described in: Y. -W. Hu and C. Mezei, *Can. J. Biochem.*, 49:320 (1971). Different compositions, including serum, serum substitutes, growth factors, such as nerve growth factor, hormones, and/or drugs can be used in the medium which are optimized for the particular nerve cell being cultured, to enhance proliferation and regeneration of nerve cells.

Differentiated cell functions expressed by cells cultured on electrically conducting substrates may be measured using specific, quantitative assays available in the art. For cell functions that require DNA synthesis, such as cell proliferation and gene transfection, optimum conditions can be identified by measuring effects on cellular DNA synthesis using standard radioactive labelling (e.g., incorporation of tritiated-thymidine) or immunocytochemical (e.g., bromodeoxyuridine uptake) methods. Effects on cell growth may also be measured by quantitating increases of cell number during culture on matrices coated with different attachment molecule densities using a Coulter Counter or colorimetric cell counting assay (e.g., acid phosphatase assay).

Morphological techniques can also be used to assess optimum conditions. For example, cells are fixed in 1% glutaraldehyde, washed with phosphate buffered saline (PBS), dehydrated in methanol, air dried, and stained with Coumassie brilliant blue. Cell shapes (projected cell areas) are quantitated by computerized morphometric analysis using an Image I Processor (Image Technology Corporation). Eight random areas are chosen and the projected cell area for every cell in the field is measured; at least 25 cells are analyzed per experimental condition. Methods available in the art can be used, such as quantitative dot-blot assay, to analyze secretion rates for proteins.

DNA synthesis may be used as a measure of potential for cellular proliferation. Cells are pulse labelled for 16 hours beginning at 48 hours post-cell attachment with $^3$H-thymidine, and subsequently fixed as outlined above. The dishes are coated with Kodak NTB2 autoradiography emulsion, and exposed for seven days. Autoradiographic grains are developed using Kodak D-19 developer. The percentage of cells actively synthesizing DNA is quantitated by choosing 8 random areas on each dish and counting those cells with nuclear grains versus the total number of cells. A minimum of 35 cells is counted per dish.

B. In Vivo Conditions

The electrically conducting polymers may be implanted in vivo into a patient in need of therapy to repair or replace damaged cells or tissue, such as nervous system tissue. Scaffolds for tissue engineering (implantable matrices) can be coated with, or made of, conducting polymers to enhance regeneration, growth or function of implanted cells or cells which migrate into, attach and proliferate within the implanted matrices. Materials which can be used for implantation include sutures, tubes, sheets, adhesion prevention devices (typically films, polymeric coatings applied as liquids which are polymerized in situ, or other physical barriers), and wound healing products (which vary according to the wound to be healed from films and coating to support structures).

To enhance the effectiveness of the treatment, compositions which further promote nervous tissue healing, such as proteins, antibodies, nerve growth factors, hormones, and attachment molecules, can be applied together with the polymer, and optionally can be covalently attached to the polymer or a polymeric support material. Those skilled in the art can readily determine exactly how to use these materials and the conditions required without undue experimentation.

VI. Application of Voltage or Current to Polymers

A voltage or current optionally is applied to the polymer in an amount effective to enhance healing of cells or tissue such as nervous tissue adhered or adjacent to the polymer, by a voltage source electrically connected to the polymer. The voltage or current applied is selected based on conditions such as the choice of polymer, growth factors or other compositions as well as the nerve cell being stimulated. For example, for polypyrrole polymers, the voltage can range between about 0 and 1 Volts, versus Ag/AgCl, and preferrably between about 10 $\mu$V to 500 mV. The current which can be applied ranges between about 10 namp to 400 $\mu$amp. The voltage or current may be applied to cells on the polypyrrole polymer, for example, for a period of time equivalent to about 10 min. to 6 hours in vivo or in vitro in a solution, for example, at about pH 7.4.

In in vivo applications, the electrically conducting polymer may be disposed on or blended with a polymeric support structure, such as a film, disc, suture, tube, sheet or scaffold for tissue engineering, which is optionally electrically connected to a source of voltage or current. Nerve or other cells may be seeded within a matrix formulated or coated with the electrically conducting polymer for implantation or they may migrate into and proliferate on and within the matrix. The electrical connection can be, for example, needles which are inserted to contact the implant, or electrodes attached to the implant prior to implantation which can be externally connected to an appropriate electrical power source.

The present invention will be further understood by reference to the following non-limiting examples.

In the examples, in vitro experiments demonstrate the ability of the conducting polymer polypyrrole to support the attachment, regeneration and differentiation of nerve cells with both neuronal cell lines and primary nerve explants. In vitro experiments also show that application of a potential across the polypyrrole film stimulates adhesion and extension of nerve cell processes. In vivo tissue response to polypyrrole is demonstrated to result in minimal inflammatory response and little to no fibrous tissue formation compared to other common FDA-approved matrices such as PLA. Also demonstrated is the lamination of PP films with polymers such as poly(lactic-co-glycolic acid) to fabricate pliable and suturable PP discs and tubes for use as implants for use in nerve regeneration therapies. The examples thus demonstrate the usefulness of conducting polymers such as polypyrrole as biomaterials for procedures requiring stimulation of nerve cells.

EXAMPLE 1

Synthesis of Polypyrrole Films

PP was synthesized by the electrochemical approach which is relatively simple and offers good control over film properties such as film thickness and uniformity. Indium Tin Oxide (ITO) conductive borosilicate glass (Delta Technologies, Still Water, Minn.) was used as the electrically conductive surface for the PP film deposition. Prior to electrochemical deposition of PP, the ITO glass slides (75× 25 mm or 50×25 mm, 40 $\Omega$/square) were cleaned thoroughly by sonication for 5 min in each of three organic solvents of increasing polarity (hexane, methanol, and methylene chloride). A three electrode setup was used for the electrochemical synthesis of PP: the ITO glass was used as the working electrode, a platinum gauze was used as the counter electrode, and a Ag/AgCl electrode (Fisher Scientific, Pittsburgh, Pa.) was used as a reference. PP film was electrochemically deposited on to the ITO glass (working electrode) at a constant potential of 0.7 volts versus Ag/AgCl reference from an aqueous solution (Milli-Q® ultra pure water) of 0.1 M pyrrole (Aldrich Chemical Co., Milwaukee, Wis.) containing 0.1 M sodium salt of poly (styrenesulfonate) (Aldrich Chemical Co.). The sodium salt of poly(styrenesulfonate) served as both the dopant and electrolyte. A Pine Instruments AFRDE4 bipotentiostat (Pine Instruments, Grove City, Pa.) was used as the source of constant voltage.

Films of two different thickness were synthesized: 0.1 to 0.15 $\mu$m (thin film) and 1.8–2.0 $\mu$m (thick film). The film thickness was controlled by the passage of charge (A. F. Diaz et al., *J. Electroanal. Chem.*, 129:115 (1981)), with a charge of 26.2 mCol/cm$^2$ yielding a polypyrrole (PP) film of approximately 0.1 $\mu$m in thickness. The amount of charge passed during the film synthesis was determined from the area under the curve of a plot of voltage versus time. This plot was obtained using a time base Linseis x-y recorder (Linseis, Germany).

PP thick films were laminated with PLGA (50:50, obtained from Medisorb, Cincinnati, Ohio) films to yield processible and suturable PP films and tubes. The PLGA films were cast from a solution (100 mg/ml) in chloroform into 30 ml beakers (1 ml per beaker, 7.55 cm$^2$). After 24 hours the films were removed from the bottom of the beakers by floating them off in water. The free floating films were then air dried for another 24 hours before further use. The PP thick film was gently peeled off the ITO glass and then floated in distilled deionized water (Milli-Q™) and, subsequently transferred onto a clean glass slide. The PP film was then wetted with methylene chloride and layered with PLGA film of desired thickness. The laminated PP films were then cut into discs of about 5 mm diameter, and about 250 to 260 $\mu$m (about 2 $\mu$m PP film thickness and about 250 $\mu$m PLGA) in thickness, for cell growth studies and implantation in rat models.

EXAMPLE 2

Culture of Nerve Cells on Polypyrrole

The PC-12 cell line, which is a well-characterized, nerve-like cell line derived from a rat pheochromocytoma (L. Greene and A. Tischler, *Proc. Natl. Acad. Sci., USA.*, 73:2424 (1976)), was used. PC-12 cells respond reversibly to nerve growth factor (NGF) by induction of the neuronal phenotype (expression of neurites). Additionally, the sciatic nerve was isolated from 16-d chick embryos as described in: Y. -W. flu and C. Mezei, *Can. J. Biochem.*, 49:320 (1971).

PC-12 cells were cultured in 85% high-glucose DMEM (GibcoBRL, Grand Island, N.Y.), 10% heat-inactivated horse serum, and 5% fetal bovine serum (FBS). Cells were maintained in a humid, 7% CO$_2$ incubator and passaged via trituration at 1:2 dilution every other day. Cells were "primed" by the addition of 25 ng/ml NGF (Boehringer-Mannheim, Indianapolis, IN) 24 h prior to seeding cells.

During experiments, cells were maintained in culture medium supplemented with 25 ng/ml NGF. Cells were seeded into wells formed by the attachment of PP/PSS films to ethanol-sterilized Plexiglas wells (1 cm×1.5 cm inner dimension) using autoclaved vacuum grease. In all experiments, 1 ml of a $2 \times 10^4$ cells/ml solution was used per well. Primary sciatic nerve explants were cultured exclusively in high glucose DMEM supplemented with glucose to 6 mg/ml, 10% FBS, 1 mM sodium pyruvate, and 25 ng/nl NGF.

Growth of Nerve Cells on Thin PP/PSS Films

Thin films of PP were examined for their ability to support nerve cell growth in vitro. Thin PP films permitted the use of light microscopy and quantitative image analysis tools to study cell-material interactions in detail. Cells were viewed under 10× or 20× magnification using an inverted phase contrast microscope (Diaphot-TMD; Nikon Inc., Garden City, N.Y.). Images from the microscope were obtained using a CCD video camera (HVC-20; Hitachi, Japan) and were subsequently digitized using NIH Image software (v1.58; National Institutes of Health, Bethesda, Md.) and a Scion image capture board (LG-3; Scion Corp., Frederick, Md.).

Figure 2A:
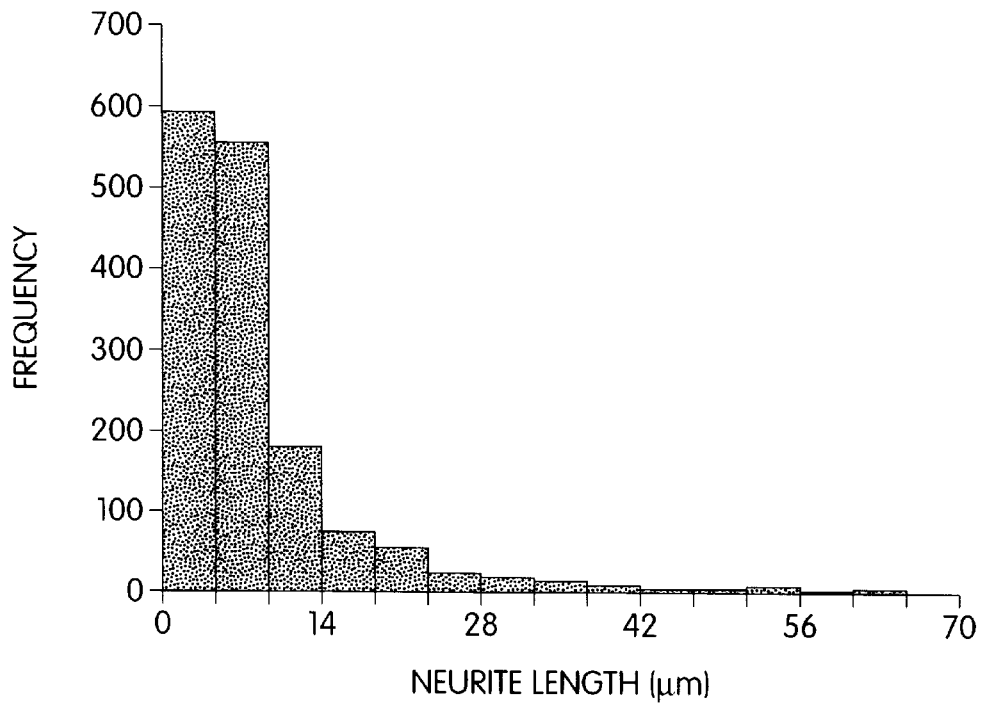
FIG. 2a is a graph of the frequency distribution of neurite lengths for PC12 cells grown for 24 hours on tissue culture polystyrene.
Figure 2B:
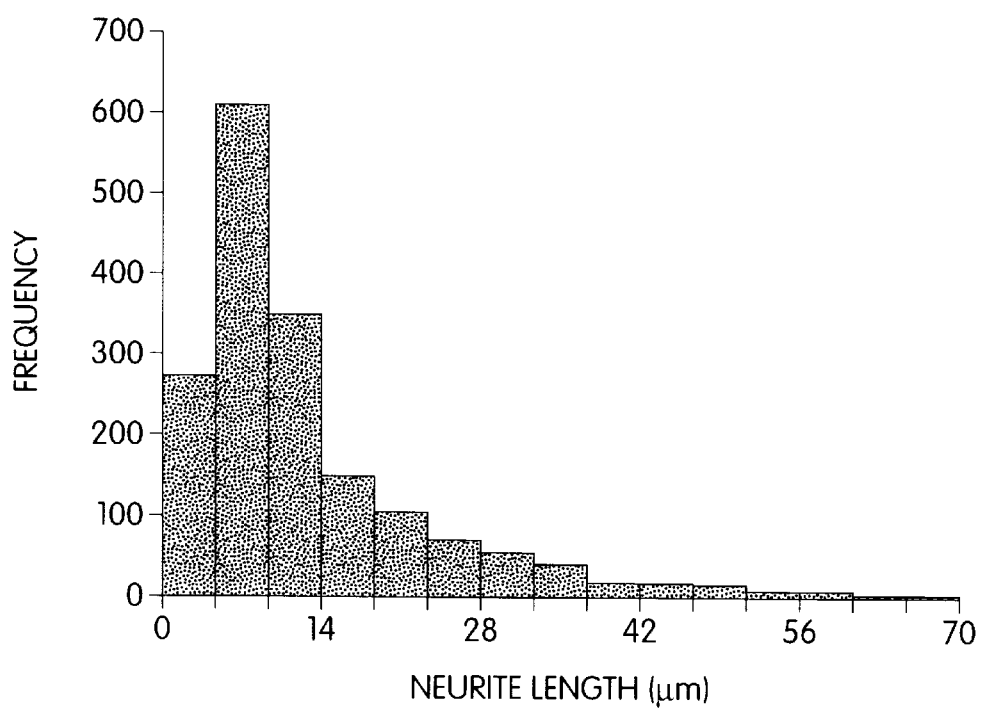
FIG. 2b is a graph of the frequency distribution of neurite lengths for PC12 cells grown for 24 hours on poly(pyrrole)/poly(styrene-sulfonate).

Phase contrast images of PC-12 cells grown for 24 hours on either tissue culture polystyrene (TCPS), polypyrrole/poly(styrene sulfonate) (PP/PSS), or poly(lactic acid) (PLA) showed that growth of cells on PLA, is poor, whereas growth on either TCPS or PP/PSS is greatly enhanced. Image analysis techniques were used to measure the lengths of individual neurites (dendrites and axons) on each cell. Length was defined as the straight line distance from the tip of a neurite to the junction between the cell body and neurite base. FIG. 2 shows the distribution of neurite lengths for cells grown for 24 h on TCPS (FIG. 2a) and PP/PSS (FIG. 2b). Each plot represents data for 10 images from each of 2 different experiments. The histograms demonstrate that neurite outgrowth on PP/PSS is improved over that on TCPS (p less than 0.001). Neurite lengths were measured using image analysis, as the distance from the tip of each neurite to the cell body. (In FIG. 2a: mean $\Delta x=10$ $\mu$m; 26% greater than 10 $\mu$m; and N=1596. In FIG. 2b: mean $\Delta x=14$ $\mu$m; 47% greater than 10 $\mu$m; and N=1775.) Scanning electron micrographs also indicated that PP was a sufficient surface for attachment and growth of the primary chick sciatic nerve explants, which include the sciatic nerve cells along with support cells (e.g., fibroblasts, Schwaan cells, etc.). Support of both neuronal and support cells is critical for nerve regeneration.

Thus, the conductive polymer polypyrrole (PP) enhances in vitro neurite extension in the neuronal-like PC-12 cell line and primary chick sympathetic nerves compared to tissue culture polystyrene (TCPS) and polylactic acid (PLA) controls. In addition, PC-12 cells interacted more uniformly with polypyrrole and displayed less cell-cell clumping compared to TCPS.

Growth of Nerve Cells on Thick PP/PSS Films

PC-12 cell interaction with thick poly(pyrrole)/poly(styrene-sulfonate) (PP/PSS) films was studied. After 3 days of growth on polymer films as described above, cells were fixed with 1% gluteraldehyde for 10 min then exposed to increasing concentrations of ethanol (50%, 60%, 80%, 90%) for 2 min each. The cells were then allowed to dry overnight. Images of cells were obtained using an environmental scanning electron microscope (ESEM) (Electro Company, Boston, Mass.) equipped with a Trecor detector set at an accelerating voltage of 15 kV under a vacuum of 4.9 torr and 6% humidity. ESEM showed that PC-12 cells attach well to the thick PP films. Weaker adhesion and a lower overall percentage of cell attachment were observed for poly(lactic-co-glycolic acid) (PLGA) controls by ESEM.

EXAMPLE 3

Electrical Stimulation and Growth of Nerve Cells on PP Thin Films

Figure 3A:
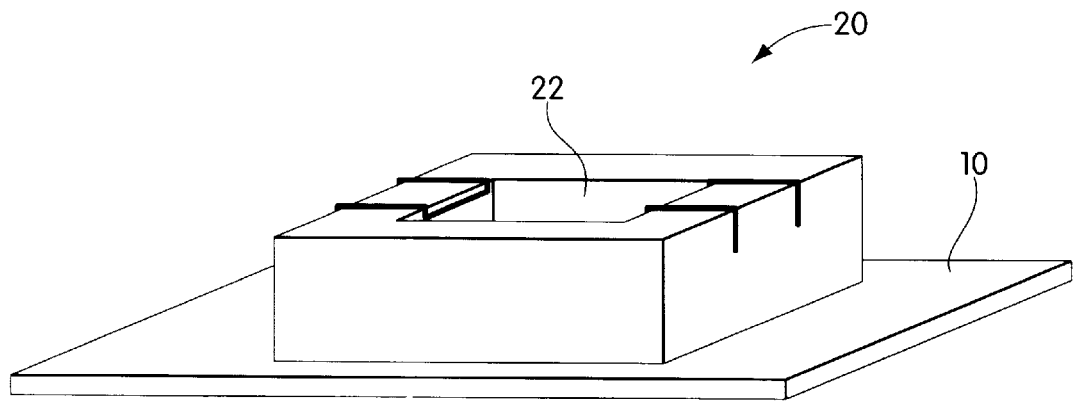
FIG. 3a is a side perspective view and FIG. 3b is a top view of a device including a chamber for the electrical stimulation of nerve cells on electrically conducting polymers.
Figure 3B:
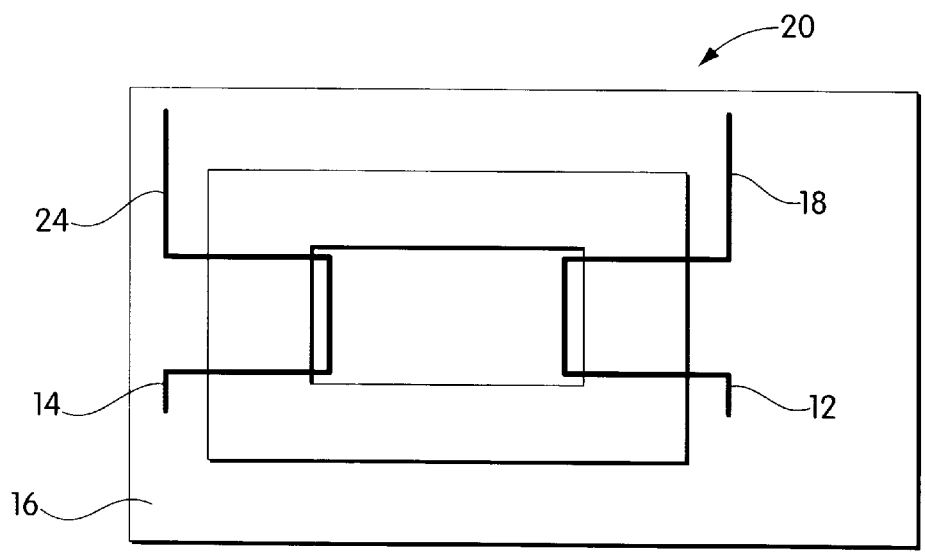

In vivo electrical stimulation of PC12 nerve cells on PP thin films was conducted in the device 20 shown in FIG. 3. Device 20 in FIG. 3 includes: chamber 22 for receiving the conductive polymer and the cells nerve cells disposed thereon; polypyrrole/ITO glass 10; Ag wire 12; Au wire 14; working electrode 16; reference electrode 18; and counter electrode 24.

Primed PC-12 cells were plated onto PP thin films at densities of 2×10 cells/ml and then incubated for 24 h to permit attachment and spreading. After this initial 24 h period, the PC-12 cells were subjected to a steady potential of 100 mV for a duration of 2 h. A bipotentiostat was used as the source of constant voltage. After electrical stimulation, the cells were incubated for an additional 24 h (a total of 48 h from the start of the experiment). ESEM images of the cells were obtained both before (24 h) and after electrical stimulation (48 h). PC-12 cells plated on PP thin films that were not subjected to any electrical stimulation served as controls. Cells that were exposed to a voltage had more pronounced neural phenotypes including many more neurites and enhanced cell spreading. The results were highly reproducible; the same results were obtained in four independent experiments, each performed in duplicate.

Figure 4A:
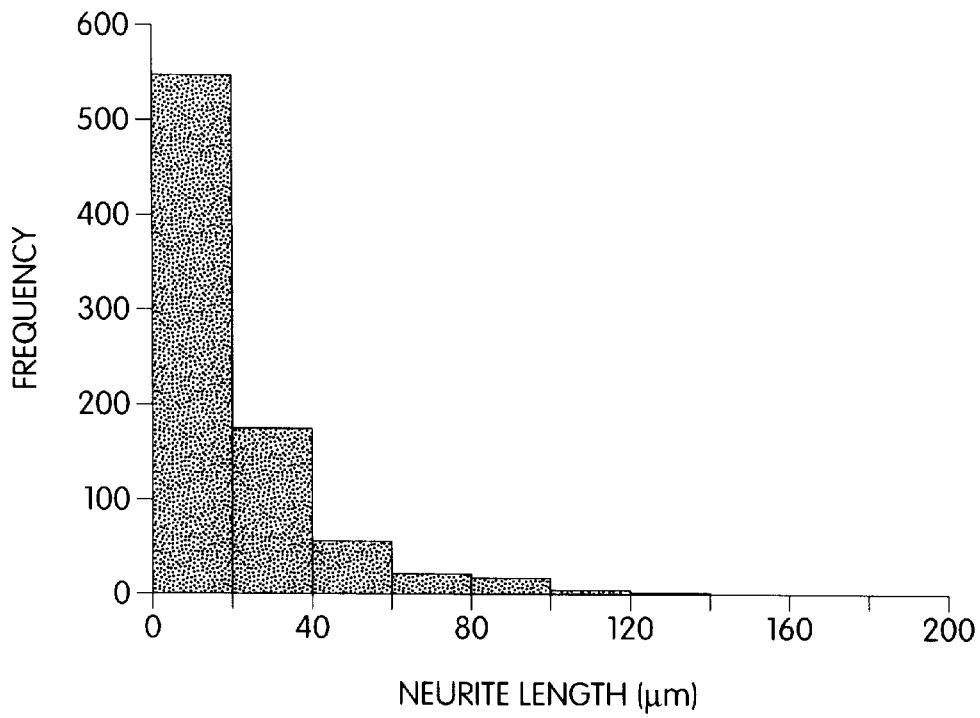
FIG. 4a is a graph of the frequency distribution of neurite lengths for PC12 cells grown and exposed to an electrical potential on poly(pyrrole)/poly(styrene-sulfonate) nearest to the counter electrode.
Figure 4B:
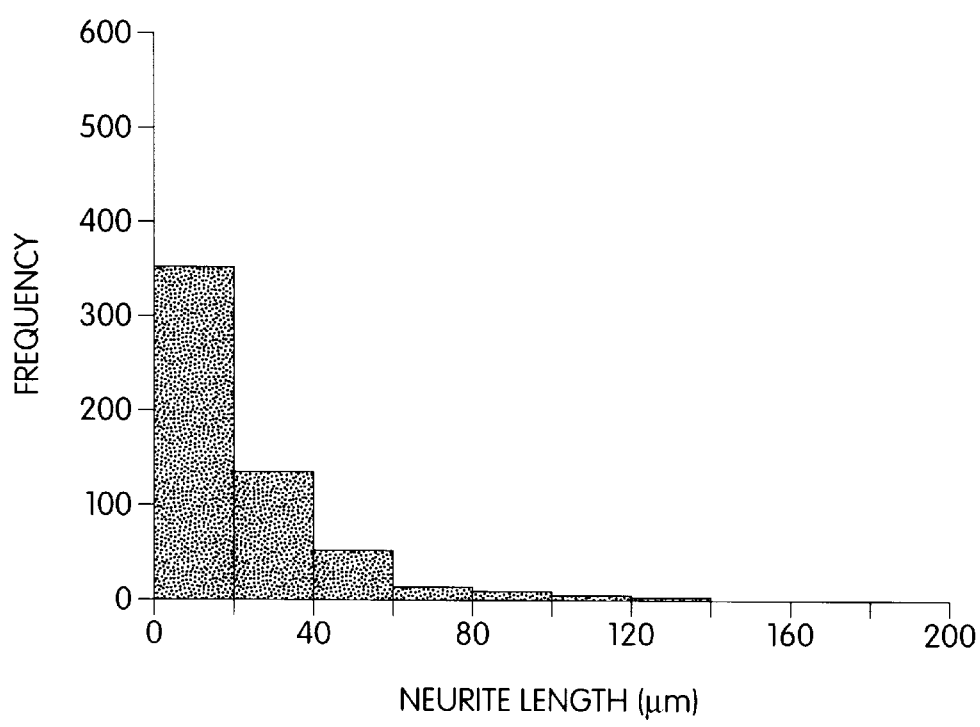
FIG. 4b is graph of the frequency distribution of neurite lengths for PC12 cells grown and exposed to an electrical potential on poly(pyrrole)/poly(styrene-sulfonate) farthest from the counter electrode.

FIG. 4 is a graph of neurite length distribution for PC12 cells grown for 48 hrs. on PP/PSS in the device shown in FIG. 3. Cells were exposed to 100 mV potential for 2 hrs. after 24 hrs. of growth. Neurite lengths were measured in the cell well along the left well edge (FIG. 4a, N total=841) defined as nearest the gold counter electrode, and along the right well edge (FIG. 4b, N total=575) farthest from the counter electrode. The counter electrode, which serves as the cathode, is the spatial position where the current density is the highest, resulting in more neurites for these cells.

Electrical resistance measurements were obtained for PP thin films and DMEM (culture medium) using a multimeter (Micronta, Radio Shack, USA) and were 1 K$\Omega$ and approximately 180 K$\Omega$ respectively. This suggests that the majority of the current should flow through the PP film which is the path of least resistance. Controls in which a voltage was passed exclusively through the medium demonstrated a negligible effect on PC12 cells grown on PP/PSS for 48 hrs. In this test, two gold wires were affixed to opposite ends of the cell well. One gold wire served as the counter electrode and the second wire served as the working electrode (typically, the ITO/PP is the working electrode). A silver wire on a third side of the well was used as a reference electrode. The results indicate that stimulation of the neuronal phenotype in PC-12 cells is the result of current passed through the polypyrrole film.

EXAMPLE 4

In Vivo Implantation of Laminated PP Thick Films

In vivo studies were conducted to determine tissue response to polypyrrole. Laminated PP/PLGA thick film discs synthesized as described in Example 1 (5 mm diameter×2 $\mu$m thickness) were implanted into male Lewis rats in subcutaneous and intramuscular locations. Films and surrounding tissue were harvested at 1, 2 and 14 weeks. At the time of polymer removal, rats were healthy with no apparent signs of inflammation at the site of implantation. H&E staining of a histological section of muscle from a 2 week implant demonstrated that inflammation associated with the PP film is less severe than that induced by the PLGA film. A Brightfield micrograph, 100× total magnification was used.

EXAMPLE 5

In Vivo Growth of Nerve Cells on PP/PLGA Conduits

The sciatic nerve of an adult male Lewis rat was transected and resected with a polypyrrole conduit. Thick PP films, laminated with a 50:50 PLGA as described in Example 1, were formed into conduits having an approximate length of 12 mm and a diameter of about 1.5 mm. The PP formed the inner lining of the conduit. A cut was made in the sciatic nerve of the left femur of an adult male Lewis rat. Approximately 1 mm of the proximal portion of the transected sciatic nerve was inserted into one end of the conduit, the conduit was filled with sterile saline, and then 1 mm of the distal portion of the transected sciatic nerve was inserted into the other end of the tube. The final gap between the distal and proximal portions of the cut nerve was about 10 mm. The tube was fixed with standard 10-0 nylon sutures. After 8 weeks, the nerve was harvested. A nerve fiber bundle extended from the distal portion of the nerve across the gap between the original two nerve stumps, thus demonstrating the ability of the polypyrrole to support nerve regeneration even though a voltage or current was not applied to the conducting polymer.

Modifications and variations of the methods and compositions described herein will be obvious to those skilled in the art from the foregoing detailed description and are intended to come within the scope of the appended claims.

We claim:

1. A method for altering the regeneration, differentiation or differentiated cell function of cells comprising:
   attaching or abutting cells to a surface comprising an electrically conducting polymer for a sufficient time to alter the regeneration, differentiation or differentiated cell function of the cells attached to or abutting the polymer, without damaging the cells,
   wherein the cells are selected from the group consisting of endothelial cells, parenchymal cells, cells forming bone or cartilage, and neurons.

2. The method of claim 1, wherein the cells are neurons.

3. The method of claim 1, wherein the cells attach to the electrically conducting polymer.

4. The method of claim 1, wherein the method further comprises applying an electric current or voltage to the polymer in an effective amount and for a sufficient time to alter the regeneration, differentiation or differentiated cell function of the cells attached or abutted to the polymer, without damaging the cells.

5. The method of claim 2 wherein the electrically conductive polymer is selected from the group consisting of polyanilines, polypyrroles, polythiophenes, and copolymers and blends thereof.

6. The method of claim 2 wherein the electrically conductive polymer is polypyrrole.

7. The method of claim 2, wherein the neurons are selected from the group consisting of naturally occurring mammalian neurons and recombinant neurons.

8. The method of claim 2, wherein the neurons are selected from the group consisting of brain, spinal, sensory, and motor neurons.

9. The method of claim 2 wherein the polymer is coated onto or blended with a polymeric support structure.

10. The method of claim 9 wherein the structure comprises a biocompatible polymer.

11. The method of claim 10 wherein the structure comprises a biodegradable polymer.

12. The method of claim 2 wherein molecules selected from the group consisting of proteins, antibodies nerve growth factors, hormones and attachment molecules are covalently attached to the electrically conductive polymer.

13. The method of claim 12 further comprising implanting with the polymer a composition which enhances healing of the nervous tissue.

14. The method of claim 2 further comprising implanting the conductive polymer into a patient in need of treatment and applying a voltage or current to the polymer in an amount effective to enhance the regeneration, differentiated cell function, or differentiation of nervous tissue comprising the neurons.

15. The method of claim 13 wherein the nervous tissue is selected from the group consisting of central and peripheral nervous system tissue.

16. The method of claim 13 comprising implanting the polymer into a patient in need of treatment and applying a voltage or current to the polymer in an amount effective to enhance regeneration of the neurons.

17. The method of claim 14 wherein the extension of neurites on the neurons is enhanced.

18. A device for altering the regeneration, differentiation or differentiated cell function of neurons comprising:
   a) an electrically conducting polymer in the form of a structure selected from the group consisting of sutures, tubes, sheets, films, and scaffolds for tissue engineering, and
   b) first and second electrodes for inducing a voltage or current across the polymer, wherein the first and second electrodes are electrically coupled with the polymer,
   wherein the device is configured and arranged to accept said neurons onto said electrically conducting polymer for a sufficient time and is capable of the alteration of regeneration, differentiation, or differentiated cell function of neurons without damaging the cells when the device is attached to or abuts neurons and an effective amount of a voltage or current to alter the regeneration, differentiation or differentiated cell function of the neurons is applied to the neurons for a sufficient time.

19. The device of claim 18 wherein the electrically conductive polymer is selected from the group consisting of polyanilines, polypyrroles, polythiophenes, and copolymers and blends thereof.

20. The device of claim 18 wherein the electrically conductive polymer comprises polypyrrole.

21. The device of claim 18 wherein the device is capable of the alteration of regeneration, differentiation, or differentiated cell function of neurons selected from the group consisting of brain, spinal, sensory and motor neurons.

22. The device of claim 18 wherein the electrically conductive polymer is coated onto or blended with a polymeric support structure.

23. The device of claim 18 wherein the structure comprises a biocompatible polymer.

24. The device of claim 18 wherein the structure comprises a biodegradable polymer.

25. The device of claim 18 further comprising a composition which stimulates neuron growth.

26. The device of claim 18, wherein the electrically conducting polymer is capable of having neurons attach thereto.

* * * * *

UNITED STATES PATENT AND TRADEMARK OFFICE
CERTIFICATE OF CORRECTION

PATENT NO. : 6,095,148
DATED : August 1, 2000
INVENTOR(S) : Venkatram R. Shastri, Christine E. Schmidt, Robert S. Langer and Joseph P. Vacanti It is certified that error appears in the above-identified patent and that said Letters Patent is hereby corrected as shown below:

<u>Title page,</u>
Item [56], FOREIGN PATENT DOCUMENTS, replace "40 26978 A1" with -- DE 40 26978 A1 --;
OTHER PUBLICATIONS, within the Kerns et al., reference title replace "Regenration" with -- Regeneration --;
Item [57], ABSTRACT, replace "The conductive polymers may implanted adjacent to or seeded with nerve cells." with -- The conductive polymers may be implanted adjacent to or seeded with nerve cells. --;

<u>Column 1,</u>
Line 17, replace "in vitro or in vivo" with -- *in vitro* or *in vivo* --;
Line 26, replace "436;165 (1987);" with -- 436:165 (1987); --

<u>Column 2,</u>
Line 5, replace "Cell-surface surface interactions" with -- Cell-surface interactions --;

<u>Column 3,</u>
Lines 5 and 20, replace "in vitro or in vivo" with -- *in vitro* or *in vivo* --;

<u>Column 4,</u>
Line 11, replace "polythiophenes," with -- "polythiophenes", --;
Line 51, replace "(1993)1." with -- (1993)]. --;
Line 60, replace "HCI" with -- HCl --;

<u>Column 6,</u>
Line 42, replace "Thin Solid Films" with -- *Thin Solid Films* --;
Line 44, replace "Institutes" with -- Institute --;
Line 44, replace "Technology" with -- Technology. --;

<u>Column 7,</u>
Line 24, replace "Institutes" with -- Institute --;

<u>Column 8,</u>
Lines 33 and 34, replace "prior to in vivo or in vivo use." with -- prior to *in vitro* or *in vivo* use. --;
Lines 35 and 36, replace "polymer can blended with" with -- polymer can be blended with --;

UNITED STATES PATENT AND TRADEMARK OFFICE
CERTIFICATE OF CORRECTION

PATENT NO. : 6,095,148
DATED : August 1, 2000
INVENTOR(S) : Venkatram R. Shastri, Christine E. Schmidt, Robert S. Langer and Joseph P. Vacanti It is certified that error appears in the above-identified patent and that said Letters Patent is hereby corrected as shown below:

Column 9,
Line 52, replace "in vitro" with -- *in vitro* --;

Column 11,
Line 53, replace "in vitro" with -- *in vitro* --;
Line 58, replace "in vitro" with -- *in vitro* --;

Column 12,
Lines 3 and 4, replace "in vitro" with -- *in vitro* --;
Line 4, replace "in vivo" with -- *in vivo* --;
Line 53, replace "In Vivo" with -- *In Vivo* --;

Column 13,
Line 26, replace "in vivo" with -- *in vivo* --;
Line 42, replace "in vitro" with -- *in vitro* --;
Line 48, replace "In vivo" with -- In vivo --;

Column 14,
Line 59, replace "Y. -W. flu" with -- Y. -W. Hu --;

Column 15,
Line 21, replace "National Institutes of Health" with -- National Institute of Health --;

Column 16,
Line 17, replace "2x10 cells/ml" with -- $2 \times 10^4$ cells/ml --;
Line 62, replace "In Vivo" with -- *In Vivo* --;
Line 63, replace "In Vivo" with -- *In vivo* --;

Column 17,
Line 12, replace "In Vivo" with -- *In Vivo* --;

UNITED STATES PATENT AND TRADEMARK OFFICE
CERTIFICATE OF CORRECTION

PATENT NO.   : 6,095,148
DATED        : August 1, 2000
INVENTOR(S)  : Venkatram R. Shastri, Christine E. Schmidt, Robert S. Langer and Joseph P. Vacanti It is certified that error appears in the above-identified patent and that said Letters Patent is hereby corrected as shown below:

Column 18,
Line 19, replace "The method of claim 13" with -- The method of claim 14 --;
Line 21, replace "The method of claim 13" with -- The method of claim 14 --; and
Line 8, replace "antibodies nerves" with -- antibodies, nerve --.

Signed and Sealed this

Seventh Day of January, 2003

JAMES E. ROGAN
*Director of the United States Patent and Trademark Office*